United States Patent [19]

Palmer et al.

[11] 3,956,406

[45] May 11, 1976

[54] PURIFICATION OF TRIMETHYLOLPROPANE

[75] Inventors: Billy W. Palmer; David L. Bondurant, both of Longview, Tex.

[73] Assignee: Eastman Kodak Company, Rochester, N.Y.

[22] Filed: Oct. 4, 1974

[21] Appl. No.: 512,826

[52] U.S. Cl. ............................................. 260/637 P
[51] Int. Cl.² ......................................... C07C 29/24
[58] Field of Search................................. 260/637 P

[56] References Cited
UNITED STATES PATENTS

| | | | |
|---|---|---|---|
| 2,806,890 | 11/1957 | Gottesman ...................... | 260/637 P |
| 2,806,891 | 11/1957 | Gottesman et al. ............. | 260/637 P |
| 3,183,274 | 5/1965 | Robeson...................... | 260/637 P X |

FOREIGN PATENTS OR APPLICATIONS

| | | | |
|---|---|---|---|
| 816,208 | 7/1959 | United Kingdom ............. | 260/637 P |

*Primary Examiner*—James O. Thomas, Jr.
*Assistant Examiner*—G. Breitenstein
*Attorney, Agent, or Firm*—Edward R. Weber; Daniel B. Reece, III

[57] ABSTRACT

Trimethylolpropane prepared in alkali solution by the condensation of n-butyraldehyde and formaldehyde is purified by extraction of the trimethylolpropane from the process effluent with a first solvent and the subsequent addition of a second solvent to the extract to further reduce the content of water and alkali salts. The first solvent may be recovered from the trimethylolpropane containing mixture by a simple distillation. The remaining mixture of trimethylolpropane and the second solvent may be separated by settling and decanting. In a preferred embodiment isobutanol is the first solvent and xylene is the second solvent.

8 Claims, No Drawings

PURIFICATION OF TRIMETHYLOLPROPANE

Trimethylolpropane is a known chemical useful in polyesters, synthetic lubricants, alkyls, urethanes and other products. Trimethylolpropane produced by the alkali catalyzed condensation of formaldehyde and n-butyraldehyde must be separated from the alkali salts prior to purification as the said alkali salts will cause decomposition of the trimethylolpropane during the subsequent purification process.

Many procedures have been proposed for this separation. Among these procedures are conventional extraction techniques employing a single solvent such as ethyl acetate, isobutyl acetate, etc. (U.S. Pat. No. 3,183,274), solvent mixtures such as ethyl acetate/ethanol, isobutanol/-toluene, or chlorinated solvents such as dichloroethane and isobutyl alcohol. These types of processes generally remove most of the trimethylolpropane but the isolated product contains more than about 500 ppm alkali and generally requires the use of from 4½ to 9 volumes of solvent per volume of aqueous feed. The solvent used must be recovered by distillation for recycle. In cases where lower volumes of solvent are used the art teaches that the trimethylolpropane must be preconcentrated to get a solution containing only about 40–45% water prior to extraction.

Another type of extraction system involves the use of an efficient solvent for the removal of trimethylolpropane from the aqueous stream followed by treatment of the extract with an ion exhcange resin to remove the alkali salts which contaminate the product (U.S. Pat. No. 3.076,854). Even after this ion exchange treatment the trimethylolpropane will contain as much as 2,000 ppm alkali. As is known in the art, the rate of decomposition of trimethylolpropane to undesirable by-products increases rapidly with increasing concentration of alkali salts and increasing temperatures.

It is, therefore, an object of this invention to provide a process wherein trimethylolpropane can be efficiently separated from the alkali salts.

Another object of the invention is to provide a process wherein relatively small volumes of solvent are required to recover the trimethylolpropane.

Yet another object of the invention is to provide a process wherein a minimum amount of processing is required to recover the trimethylolpropane from the solvent.

These and other objects and advantages of this invention will become apparent from the following description and appended claims.

In the process of the instant invention the aqueous alkaline process stream from the condensation of n-butyraldehyde and formaldehyde is extracted with a first solvent and the resulting mixture of TMP and the first solvent is combined with a second solvent which second solvent serves to further reduce the aqueous alkaline content of the extract.

The first solvent can be any solvent which is immiscible in the trimethylolpropane containing aqueous alkaline process stream, which possesses a strong affinity for TMP and which can be conveniently separated from the second solvent. In a preferred embodiment the first solvent will have a lower boiling point than the trimethylolpropane and the second solvent and therefore can be separated conveniently by distillation. Suitable solvents include lower boiling aliphatic alcohols such as isopropanol, iso-butanol, n-butanol and lower molecular weight esters of alcohols and ether alcohols such ehtyl acetate, and ethylene glycol monomethyl ether acetate.

The second solvent must possess two characteristics. It should be substantially immiscible with water and easily separated from the first solvent and trimethylolpropane. In a preferred embodiment the second solvent will have a higher boiling point than the first solvent so that the first solvent may be readily removed by distillation. In another embodiment, trimethylolpropane should be soluble in the solvent at elevated temperatures but substantially insoluble in the solvent at ambient temperature. The second solvent can, therefore, be any straight-or branched-chain alkyl, alkenyl, aryl, aralkyl, or aralkenyl hydrocarbon, ether, ester, ketone, or halogenated derivative of these compounds so long as it meets the above requirements. Examples of suitable solvents are toluene, xylene, mesitylene, heptane, nonane, dibutyl ether, isobutyl isobutyrate, methylisoamylketone, perchloroethylene, or chlorobenzene.

The ratio of the first and second solvents with respect to each other and with respect to the process feed, can be varied considerably depending upon the composition of the aqueous alkaline trimethylolpropane containing process stream and the level of alkali contamination which is acceptable in the product trimethylolpropane. In general, increasing the amount of the first solvent used will result in an increase in extraction efficiency coupled with an increase in the amount of alkali retained in the trimethylpropane while an increase in the second solvent will result in a decrease in the amount of alkali in the extract. Increasing the amounts of either or both solvents used in relation to the feed stream increases the total volume of material to be handled with concomitant increase in equipment size and process cost. The process of the instant invention is oprable where from about 0.5 to about 4 volumes of the first solvent are used per volume of aqueous alkali feed material and about 0.5 to. about 3.0 volumes of said second solvent are used per volume of first solvent. Very good results are obtained when two volumes of the said first solvent are used per volume of aqueous alkali feed material and one volume of the said second solvent is used per volume of first solvent.

The temperature and pressure at which the extraction is carried out are not critical, although atmospheric pressure is preferred because of the obvious economies of operation presented. Temperature can be any temperature below the boiling point of the lowest boiling component present in the extraction operation and above the highest melting point, i.e., all components are in the liquid phase.

The extraction can be carried out in either a single column or in two separate columns connected in series. Where two columns are used the aqueous alkali trimethylolpropane containing feed material will be fed near the top of the first column and the first solvent will be fed near the bottom of the first column. A stream comprising the first solvent, trimethylolpropane, some water and some dissolved alkali salts is removed from the top of the first column. A waste stream comprising water and alkali salts is removed from the bottom of the first column. The second solvent is then added to the stream removed from the top of the first column, which combined stream is injected near the midpoint of the second column. A small stream of water may be injected near the top of the second column as a secondary wash to further reduce the alkali content of the effluent. A stream comprising the first solvent, the second solvent, and trimethylolpropane is removed from the top of the second column and a stream comprising water, alkali salts, and residual traces of trimethylolpropane is removed from the bottom of the second column. This stream can be recycled to the first column if desired. In a preferred embodiment, the two steps are combined in one tubular type liquid extractor. In this preferred embodiment the extractor is operated at atmospheric pressure and approximately 65°C. Two volumes of a first solvent, preferably isobutanol, are injected near the bottom of the extractor for each volume of trimethylolpropane containing aqueous alkali feed which is injected at or above the middle of the extractor. Feed rates are controlled so as to maintain the interface between the isobutanol/trimethylolpropane extract and the aqueous alkali raffinate below the point of trimethylolpropane feed. The second solvent, in this instance preferably xylene, is injected at a point equal to or above the feed point of the impurre trimethylolpropane in a quantity equivalent to one volume of solvent per volume of first solvent used. If used, the secondary water wash will be injected near the top of the column. The xylene serves to reduce the alkali salt concentration and water content of the organic phase. The resultant isobutanol/xylene/trimethylolpropane extract is recovered from the top of the extractor. After decanting away entrained water the three component organic mixture may be distilled with the isobutanol being recovered overhead for reuse. The base stream from the distillation column consisting of trimethylolpropane and xylene may then be allowed to cool whereupon the trimethylolpropane will separate out. The decanted xylene can be reused without additional processing.

Utilizing this recovery system trimethylolpropane has been separated from the aqueous alkali mixtures in quantitative yields and containing less than 50 ppm of alkali. Such material is suitable for conventional distillation and passes all commercial product specifications following distillation.

Mixed solvent systems have been previously used but this method of using a very efficient solvent to separate the trimethylolpropane from the water and alkali salts followed by treatment with another solvent to completely remove the salts and water is a unique process not previously described. Separation of the second solvent without distilltion means that one-half the solvent used does not have to be distilled. This reduces both equipment costs and operating costs.

The novelty of the unique process of this invention is further exemplified by the fact that a 50/50 mixture of xylene and isobutanol will not quantitatively separate the trimethylolpropane from the aqueous solution when 4 volumes of the solvent mixture are used per aqueous volume. It is, therefore, unobvious that utilizing identical volumes of the solvents separately as described in the instant invention would quantitatively recover the trimethylolpropane and that such efficient separation from the alkali metal salts would be obtained.

The process of the instant invention is illustrated in greater detail by the following examples. It will be understood, however, that these examples are not intended to limit the invention in any way and obvious modifications will appear to those skilled in the art.

EXAMPLE 1 - Extraction of Trimethylolpropane from a Known Mixture

In this example the isobutanol-xylene extraction system previously described is used to extract and purify trimethylolpropane from a known mixture simulating the effluent from the condensation reaction. A mixture is made up to contain 14.1 weight percent trimethylolpropane, 11.1 weight percent sodium carbonate, and 4.8 weight percent formic acid which is converted to sodium formate. The remainder of he solution is water. The extractor is a 3-inch diameter, 8-foot tall column packed with ¼-inch perforated stainless steel packing. A secondary water wash is injected one foot from the top, the raw feed and xylene feed point is two feet from the top, and the isobutanol feed point is one foot from the bottom. The extractor is run at 68°C. and atmospheric pressure. An extract stream is removed at the top of the extractor and a raffinate stream is removed from the bottom of the extractor. The extract stream is passed into a distillation column wherein the isobutanol is removed as an overhead stream. The bottom stream from the distillation column is passed to a decanter where it is allowed to cool. Xylene is removed as the upper phase in the decanter and trimethylolpropane is removed as the lower phase.

Seven hundred seventy-seven grams per hour of the synthetic process feed is fed to the extractor. This material is introducing trimethylolpropane to the extractor at 110 grams per hour. The secondary water was is fed at 7 grams per hour. The isobutanol solvent stream is flowing at 1130 grams per hour and the xylene stream is flowing at 1140 grams per hour. Ninety-nine percent of the trimethylolpropane, 109 grams per hour, is recovered as pure product. No trace of trimethylolpropane is observed by gas chromatography in the water phase raffinate. The decanted material is 90 percent trimethylolpropane and contains only 42 ppm sodium. Overall weight accountability is 99 percent while trimethylolpropane accountability is virtually 100 percent. The usable trimethylolpropane recovered by this system is essentially quantitative with the amount fed in, and the product passes commercial specifications.

EXAMPLE 2 - Extraction of Trimethylolpropane from a Reaction Mixture

A reactor effluent mixture containing trimethylolpropane synthesized by the condensation of n-butyraldehyde and formaldehyde in the presence of an alkali condensing agent is processed by the extraction unit described in Example 1. Feed streams are 765 grams per hour of reactor product and 7 grams per hour of secondary water wash.

The feed stream has a typical analysis of 13 percent trimethylolpropane, 68 percent water, 3 percent high boilers and other by-products, 8 percent sodium formate and 8 percent sodium bicarbonate. The isobutanol stream introduced into the extractor is 900 grams per hour, and the xylene stream introduced into the extractor is 1140 grams per hour. The extractor is operated at 68°C. and atmospheric pressure. Average residence time in the extractor is one hour. One hundred grams per hour of trimethylolpropane is obtained as pure, refined product. Overall weight accountability is 99 percent.

The following example illustrates the fact that four volumes of solvent per volume of aqueous stream is not as efficient as operating under the preferred operating conditions.

EXAMPLE 3

Four volumes of 75% iBuOH/25% toluene are fed to the extractor for each volume of trimethylolpropane containing solution. The feed material has the same composition as described for Example 2. The extractor is a 2 inch diameter glass tube 5½ feet tall. It operates at atmospheric pressure and 65°–69°C. Residence time is one hour. The aqueous raffinate phase from this example still contains aproximately 3% of the trimethylolpropane. The amount of alkali in the extract is 1600 PPM based on trimethylolpropane.

In a similar experiment in which 8 volumes of solvent per volume of trimethylolpropane feed are used all the trimethylolpropane is contained in the extract.

The substitution of xylene for toluene has no effect on the extractive properties of the liquid. The change from 75% i-butanol/25% toluene to 50/50 mixtures renders the solvent less efficient and therefore at a 4:1 ratio leaves more trimethylolpropane unextracted. These results indicate that a mixture of solvents is not as efficient as operating with the configuration of the instant invention.

Although the invention has been described in considerable detail with particular reference to certain preferred embodiments thereof, variations and modifications can be effected within the spirit and scope of the invention as described hereinabove and as defined in the appended claims.

We claim:

1. A proces for the purification of trimethylolpropane prepared by the condensation of n-butyraldehyde and formaldehyde in the presence of an aqueous alkali reaction medium which consists of the following steps:
    1. extracting the trimethylolpropane from the aqueous alkali medium by the addition of 2 volumes of isobutanol per volume of aqueous alkali feed;
    2. diluting the isobutanol/trimethylolpropane extract with 1 volume of xylene per volume of isobutanol initially used;
    3. distilling the xylene/isobutanol/trimethylolpropane so as to recover the isobutanol as an overhead stream;
    4. cooling the xylene trimethylolpropane bottom stream from the aforementioned distillation step so as to allow the trimethylolpropane to separate from the xylene.

2. A process according to claim 1 wherein the isobutanol recovered from the distillation column is recycled to the extraction step.

3. A process of claim 1 wherein the xylene separated from the trimethylolpropane is recycled to the extraction step.

4. A process for the purification of trimethylolpropane prepared by the condensation of n-butyraldehyde and formaldehyde in the presence of an aqueous alkali reaction medium which consists of the following steps:
    1. extracting the trimethylolpropane from the aqueous alkali medium by the addition of a first solvent selected from the group consisting of isopropanol, isobutanol, n-butanol, ethyl acetate, and ethylene glycol monomethyl ether acetate, which said solvent is immiscible in the trimethylolpropane containing aqueous alkali stream and possesses a strong afffinity for trimethylolpropane;
    2. diluting the extract which comprises said first solvent and trimethylolpropane with a second solvent selected from the group consisting of toluene, xylene, mesitylene, heptane, nonane, dibutyl ether, isobutyl isobutyrate, methyl isoamylketone, perchloroethylene, and chlorobenzene, which said second solvent is immiscible with water and easily separated from said first solvent and from trimethylolpropane individually;
    3. wherein the first solvent is used in an amount of about 0.5 to about 4.0 volumes of solvent per volume of aqueous alkali feed material and wherein the second solvent is used in an amount of about 0.5 to about 3.0 volumes of said second solvent per volume of first solvent used.

5. A process according to claim 4 wherein the first solvent has a boiling point lower than the boiling point of the second solvent.

6. A process according to claim 5 wherein the first solvent is separated from the mixed stream comprising the first solvent, the second solvent, and trimethylolpropane by distillation.

7. A process according to claim 4 wherein the trimethylolpropane is readily soluble in the second solvent at a first temperature but only slightly soluble at a second temperature which second temperature is lower than said first temperature.

8. A process according to claim 7 wherein the trimethylolpropane is separated from the second solvent, following the removal of the first solvent, by cooling the mixture and permitting the trimethylolpropane to separate out.

\* \* \* \* \*